United States Patent [19]
Costantini et al.

[11] Patent Number: 5,149,888
[45] Date of Patent: Sep. 22, 1992

[54] HYDROXYLATION OF PHENOLS/PHENOL ETHERS

[75] Inventors: Michel Costantini, Lyons; Eric Garcin, Montrouge; Michel Gubelmann, Lyons; Jean-Michel Popa, Drancy, all of France

[73] Assignee: Rone-Poulenc Chimie, Courbevoie, France

[21] Appl. No.: 486,429

[22] Filed: Feb. 28, 1990

[30] Foreign Application Priority Data

Feb. 28, 1989 [FR] France ................. 89 02868

[51] Int. Cl.$^5$ ............... C07C 37/60; C07C 41/26
[52] U.S. Cl. ......................... 568/771; 568/629; 568/638; 568/643; 568/644; 568/646; 568/650; 568/651; 568/652; 568/653; 568/743; 568/747; 568/766; 568/768
[58] Field of Search ............ 568/629, 700, 715, 643, 568/644, 646, 650, 651, 652, 743, 747, 771, 638, 653, 768, 766

[56] References Cited

U.S. PATENT DOCUMENTS 3,110,653  11/1963  Montarnal et al. ............... 204/154

FOREIGN PATENT DOCUMENTS 0200260  11/1986  European Pat. Off. .
0226257   6/1987  European Pat. Off. .
2071071  12/1979  United Kingdom .
2083816   9/1981  United Kingdom .
2116974  10/1983  United Kingdom .

OTHER PUBLICATIONS

Chemistry Letters No. 8, 1981, pp. 1053–1056, Chemical Society of Japan, Tokyo, Japan, M. Fujihira et al.: "Heterogeneous Photocatalytic oxidation of aromatic compounds on semiconductor materials: the photo-fenton type reaction"* en entier *.

Primary Examiner—Marianne M. Cintins
Assistant Examiner—Margaret J. Argo
Attorney, Agent, or Firm—Burns, Doane, Swecker & Mathis

[57] ABSTRACT

The phenols and phenol ethers, e.g., phenol itself, are effectively hydroxylated by reacting hydrogen peroxide therewith, in the presence of a catalytically effective amount of titanium dioxide.

20 Claims, No Drawings

HYDROXYLATION OF PHENOLS/PHENOL ETHERS

BACKGROUND OF THE INVENTION

1. Field of the Invention

The present invention relates to a process for the hydroxylation of phenols or phenol ethers, and, more especially, to the hydroxylation of phenols/phenol ethers by reaction with hydrogen peroxide in the presence of a catalytically effective amount of titanium dioxide.

2. Description of the Prior Art

The hydroxylation of phenol or substituted phenols utilizing hydrogen peroxide, to prepare diphenols, is a known reaction.

French Patent No. 69/45,467, published under No. 2,071,464, describes a process in which the reaction is catalyzed by a strong acid such as, for example, perchloric acid or sulfuric acid.

German Patent No. 2,410,742 describes a process similar to the above, wherein the hydrogen peroxide is employed in the form of a virtually anhydrous organic solution.

These two processes are of considerable interest, and the first is carried out industrially.

In recent years, however, attempts have been made to catalyze the hydroxylation reaction using solids that are not dissolved in the reaction medium, in order to simplify their separation from said medium of reaction and to permit their possible recycling, as well as to avoid the by-product salts which are in most cases formed during the removal of dissolved acid catalysts.

Thus, French Patent Application No. 81/17,023 (published under No. 2,489,816) describes the use of titanium silicalite as a heterogeneous catalyst in the hydroxylation of aromatic compounds by reaction of hydrogen peroxide therewith.

The small size of the particles of the catalyst used renders their separation from the reaction medium very difficult and causes problems in the recycling thereof, even though it is essential in an industrial process to recycle a costly catalyst.

In order to overcome this problem of catalyst separation, it has been proposed, in European Patent Application published under No. 200,260, to use agglomerates of these fine particles of titanium silicalite.

It has also been proposed, in European Patent Application EP-A-0,299,893, to use bridged clays as such hydroxylation catalysts. Even though interesting results are obtained by conducting the process in such manner, research on the heterogeneous catalysis of the hydroxylation of phenols or phenol ethers using hydrogen peroxide is continuing.

SUMMARY OF THE INVENTION

Accordingly, a major object of the present invention is the provision of an improved process for the hydroxylation of phenols or phenol ethers of the general formula (I):

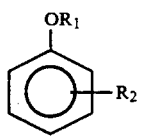

(I)

in which $R_1$ is a hydrogen atom, or a methyl, ethyl or phenyl radical, and $R_2$ is a hydrogen atom, an alkyl radical having from 1 to 4 carbon atoms, an alkoxy radical having from 1 to 4 carbon atoms or a phenyl or cyclohexyl radical, comprising reacting such phenol/phenol ether of formula (I) with hydrogen peroxide, in the presence of a catalytically effective amount of titanium dioxide.

DETAILED DESCRIPTION OF THE PREFERRED EMBODIMENTS OF THE INVENTION

More particularly according to the present invention, there are several natural and synthetic forms of titanium dioxide which can thus be used.

Thus, anatase titanium dioxide, rutile titanium dioxide and brookite titanium dioxide can be employed, even though the latter form is rare because of its narrow range of thermal stability.

Natural titanium dioxide can be used as the catalyst but, most typically, the synthetically produced titanium dioxides are used, which are commercially available.

It can also be prepared from minerals such as ilmenite.

The titanium dioxide can also be subjected to a pretreatment prior to its use as a catalyst in the hydroxylation process of the invention.

Thus, it can be calcined for one to several hours at a temperature of from about 300° C. to 1,000° C. and preferably from 300° C. to 700° C. A titanium dioxide of a different structure can also be produced, for example, by reacting anatase $TiO_2$ with potassium nitrate at an elevated temperature (above 800° C.) to form potassium titanate, hot hydrolysis of the titanate obtained and its calcination at a temperature of from about 400° to 600° C.

The titanium dioxide can be used in widely diverse forms: powder or shaped articles such as pellets (for example cylinders or trilobes), spheres or monoliths (blocks of honeycomb form) which are produced by extrusion, molding, sintering or any other type of known process.

In practice, the forms of pellets, spheres and monoliths are the most advantageous, both with respect to effectiveness, because the active sites of the catalyst are more easily reached by diffusion of the reactants, and with respect to ease of handling.

The phenols and phenol ethers which are preferably used in the process of the invention are the compounds of the formula (I) in which $R_1$ is a hydrogen atom, or a methyl or ethyl radical, and $R_2$ is a hydrogen atom, a methyl, ethyl or tert.-butyl radical, or a methoxy or ethoxy radical.

Phenol, anisole, orthocresol, metacresol, paracresol, 4-tert.-butylphenol, 2-methoxyphenol and 4-methoxyphenol are representative of such compounds of formula (I).

The process according to the invention is particularly well suited for converting phenol into hydroquinone and pyrocatechol.

It will be appreciated that the pyrocatechol/hydroquinone ratio obtained is most typically greater than 2, which is of particular interest in light of the existing markets for these two particular diphenols.

It is even possible to obtain pyrocatechol/hydroquinone ratios greater than 3.

The hydrogen peroxide can be used in the form of an aqueous solution, generally having a hydrogen peroxide concentration greater than 20% by weight. The hydrogen peroxide can also be used in the form of a solution in an organic solvent. Exemplary organic solvents for the hydrogen peroxide include the esters such as especially the alkyl or cycloalkyl esters of saturated aliphatic carboxylic acids; preferably, alkyl acetates and propionates having from 4 to 8 total carbon atoms, or mixtures thereof, will be employed. It is also possible to use solutions of hydrogen peroxide in an ether such as, for example, dioxane, diisopropyl ether or methyl tert.-butyl ether.

The compound of the formula (I)/hydrogen peroxide molar ratio generally ranges from 25/i to 3/1 and preferably from 20/1 to 4/1.

The amount of titanium dioxide described above can vary over very wide limits in the process of the present invention.

If the process is carried out discontinuously, the catalyst can constitute 0.1% to 20% by weight relative to the compound of the formula (I) employed. Preferably, this ratio by weight will range from 0.5% to 10%. If the process is carried out continuously, however, for example by reacting a mixture of the compound (I) and a solution of hydrogen peroxide over a fixed bed of catalyst or over a monolith, these catalyst/compound (I) ratios are no longer meaningful and, at any given instant, a weight excess of catalyst relative to the compound (I) can be present.

It is also possible to carry out the hydroxylation reaction of the compound (I) in a solvent for compound (I), which solvent is preferably miscible or partially miscible with water.

Exemplary of such solvents are water, alcohols such as methanol, tert.-butanol, isopropanol or ethanol, ketones such as acetone or methyl isobutyl ketone, nitriles such as acetonitrile, carboxylic acids such as acetic acid, esters such as propyl acetate, ethers such as methyl tert.-butyl ether, aprotic polar solvents such as tetrahydrothiophene dioxide (sulfolan), ethylene glycol carbonate, propylene glycol carbonate and N-methylpyrrolidone.

The temperature at which the reaction is carried out typically ranges from 45° to 160° C. under atmospheric pressure. It is also possible to carry out the reaction at a higher temperature and at a pressure higher than atmospheric pressure.

In order to further illustrate the present invention and the advantages thereof, the following specific examples are given, it being understood that same are intended only as illustrative and in nowise limitative.

In said examples to follow, the respective catalysts employed were prepared as described immediately below:

I. $TiO_2$ (I)B of BET=6 $m^2/g$:

Potassium nitrate and anatase titanium dioxide were reacted at 1,000° C. to prepare potassium tetratitanate, $K_2Ti_4O_9$.

This potassium tetratitanate was then hydrolyzed hot and subsequently calcined at 500° C. to produce $TiO_2$ (I)B having a specific BET surface area of 6 $m^2/g$.

II. $TiO_2$ (II)B of BET=62 $m^2/g$:

Potassium nitrate and anatase titanium dioxide were reacted at 1,000° C. to prepare potassium tetratitanate, $K_2Ti_4O_9$.

This potassium tetratitanate was then hydrolyzed hot, calcined at 500° C. and subsequently ground to produce $TiO_2$ (II)B having a specific BET surface area of 62 $m^2/g$.

III. RUTILE $TiO_2$ (III) of BET=23 $m^2/g$:

Titanium oxychloride was hydrolyzed. The solution obtained was washed by decantation and filtered, and then dried for 24 hours in an oven at 120° C.

IV. ANATASE $TiO_2$ (IV) of BET=4 $m^2/g$:

$TiO_2$ (I)B prepared in I was calcined at 650° C. This produced ANATASE $TiO_2$ (IV) having a specific BET surface area of 4 $m^2/g$.

V. ANATASE $TiO_2$ (V) of BET=208 $m^2/g$:

Ilmenite was disintegrated with sulfuric acid in conventional manner. To the titanium dioxide suspension obtained after hydrolysis and filtration, and containing sulfate anions in such amount that the $SO_4/TiO_2$ ratio by weight was equal to 0.08, calcium hydroxide was added in such manner that 90% of the sulfates reacted.

The suspension was then spray-dried.

This produced ANATASE $TiO_2$ (V) having a specific BET surface area of 208 $m^2/g$.

VI. ANATASE $TiO_2$ (VI) of BET=212 $m^2/g$:

Ilmenite was disintegrated with sulfuric acid in conventional manner. To the titanium dioxide suspension obtained after hydrolysis and filtration, and containing sulfate anions in such amount that the $SO_4/TiO_2$ ratio by weight was equal to 0.08, calcium hydroxide was added in such manner than 120% of the sulfates reacted.

The suspension was then spray-dried.

This produced ANATASE $TiO_2$ (VI) having a specific BET surface area of 212 $m^2/g$.

VII. ANATASE $TiO_2$ (VII) of BET=286 $m^2/g$:

Ilmenite was disintegrated with sulfuric acid in conventional manner. The titanium dioxide suspension obtained after hydrolysis and filtration was washed with a 2 N ammonia solution in such manner that the $SO_4/TiO_2$ ratio by weight was equal to 0.06.

The suspension was then spray-dried.

This produced ANATASE $TiO_2$ (VII) having a specific BET surface area of 286 $m^2/g$.

VIII. ANATASE $TiO_2$ (VIII) of BET=105 $m^2/g$:

Ilmenite was disintegrated with sulfuric acid in conventional manner. The titanium dioxide suspension obtained after hydrolysis and filtration was washed with a 2 N ammonia solution in such manner that the $SO_4/TiO_2$ ratio by weight was equal to 0.0001.

The suspension was then spray-dried.

The product was calcined for 3 hours at 400° C.

This produced ANATASE $TiO_2$ (VIII) having a specific BET surface area of 105 $m^2/g$ and a sulfate ion content at the surface of 0.01%.

IX. ANATASE $TiO_2$ (IX) of BET=237 $m^2/g$:

Ilmenite was disintegrated with sulfuric acid in conventional manner. The titanium dioxide suspension obtained after hydrolysis and filtration was washed with a 2 N ammonia solution in such manner that the $SO_4/TiO_2$ ratio by weight was equal to 0.01.

The suspension was then spray-dried.

This produced ANATASE $TiO_2$ (IX) having a specific BET surface area of 237 $m^2/g$.

X. ANATASE $TiO_2$ (X):

Ilmenite was disintegrated with sulfuric acid in conventional manner. To the titanium dioxide suspension obtained after hydrolysis and filtration, and containing sulfate anions in such amount that the $SO_4/TiO_2$ ratio by weight was equal to 0.08, calcium hydroxide was added in such a way that 90% of the sulfates reacted.

The suspension was then spray-dried and subsequently calcined for 3 hours at 400° C.

This produced ANATASE $TiO_2$ (X) having a sulfate ion content at the surface of 7 to 8% and a specific BET surface area of 190 $m^2/g$.

EXAMPLES 1 TO 13

Into a 30 cm³ Pyrex glass reactor fitted with a central bar magnet stirrer, a condenser connected to a gas holder, a controlled heating system and an injection system, 9.4 g of phenol (0.10 mol) and 0.25 g of titanium dioxide were charged, after previously purging the apparatus with nitrogen.

The mixture was heated to 80° C. under stirring, and an aqueous 70% weight by weight $H_2O_2$ solution was then injected therein (0.0050 mol of $H_2O_2$).

The mixture was then permitted to react for 2 hours and 30 minutes.

After filtering off the catalyst, unconverted $H_2O_2$ was analyzed iodometrically and the diphenols were analyzed by high-performance liquid chromatography (HPLC).

In this manner, the following values were determined for each example:
(i) the $H_2O_2$ conversion rate (CR);
(ii) the yield of pyrocatechol relative to $H_2O_2$ converted (Y/PC);
(iii) the yield of hydroquinone relative to $H_2O_2$ converted (Y/HQ);
(iv) the total yield of diphenols.

The catalyst used and the results obtained in each example are reported in Table 1 which follows:

EXAMPLES 14 TO 17

4.7 g of phenol (0.05 mol), 0.25 g of ANATASE $TiO_2$ (VIII) of BET 105 m²/g, calcined for 3 hours at 400° C., and 4.7 g of solvent (see Table 2 below) were charged into a 30 cm³ Pyrex glass reactor fitted with a central bar magnet stirrer, a condenser connected to a gas holder, a controlled heating system and an injection system, after previously purging the apparatus with nitrogen.

The mixture was heated to 100° C. under stirring, and an aqueous 70% weight by weight $H_2O_2$ solution was then injected therein (0.0025 mol of $H_2O_2$).

The mixture was then permitted to react for 2 hours and 30 minutes.

After filtering off the catalyst, unconverted $H_2O_2$ was analyzed iodometrically and the diphenols were analyzed by high-performance liquid chromatography (HPLC).

The results obtained are reported in Table 2 below.

TABLE 2

| EXAMPLES | SOLVENTS | % CR of $H_2O_2$ | % Y of PC | % Y of HQ | % Y of diphenols | PC/HQ ratio |
|---|---|---|---|---|---|---|
| 14 | Acetic acid | 90.0 | 31.5 | 10.0 | 41.5 | 3.1 |
| 15 | Acetonitrile | 91.5 | 37.0 | 5.5 | 42.5 | 6.7 |
| 16 | Methyl isobutyl ketone | 52.5 | 27.0 | 4.5 | 31.5 | 6.0 |
| 17 | Sulfolan | 96.0 | 33.5 | 8.5 | 42.0 | 3.9 |

EXAMPLE 18

The procedure of Example 10 was repeated, but adding 0.412 g (0.2 mmol) of 1-hydroxyethane tetrahydrogen diphosphate.

After the addition of $H_2O_2$, the mixture was permitted to react for 20 hours at 80° C.

The following results were obtained:

TABLE 1

| EXAMPLES | CATALYSTS | % CR of $H_2O_2$ | % Y of PC | % Y of HQ | % Y of diphenols | PC/HQ |
|---|---|---|---|---|---|---|
| 1 | $TiO_2$ (I)B of BET = 6 m²/g | 46.5 | 11.0 | 0.5 | 11.5 | 22 |
| 2 | $TiO_2$ (II)B of BET = 62 m²/g calcined for 3 hours at 400° C. | 96.5 | 12.5 | 6.5 | 19.0 | 1.9 |
| 3 | RUTILE $TiO_2$ (III) of BET = 23 m²/g | 97.5 | 9.5 | 4.5 | 14.0 | 2.1 |
| 4 | ANATASE $TiO_2$ (IV) of BET = 4 m²/g calcined for 3 hours at 400° C. | 41.5 | 11.0 | 3.0 | 14.0 | 3.6 |
| 5 | ANATASE $TiO_2$ (V) of BET = 208 m²/g | 99.0 | 9.5 | 2.5 | 12.0 | 3.8 |
| 6 | ANATASE $TiO_2$ (V) of BET = 208 m²/g calcined for 5 hours at 550° C. | 97.5 | 33.0 | 8.0 | 41.0 | 4.1 |
| 7 | ANATASE $TiO_2$ (IV) of BET = 212 m²/g calcined at 5 hours at 550° C. | 88.0 | 35.5 | 6.5 | 42.0 | 5.5 |
| 8 | ANATASE $TiO_2$ (VII) of BET = 286 m²/g | 98.5 | 15.0 | 5.5 | 20.5 | 2.7 |
| 9 | ANATASE $TiO_2$ (VII) of BET = 286 m²/g calcined for 5 hours at 550° C. | 99.5 | 29.0 | 9.5 | 38.5 | 3.0 |
| 10 | ANATASE $TiO_2$ (VIII) of BET = 105 m²/g calcined for 3 hours at 400° C. | 75.5 | 35.0 | 9.5 | 44.5 | 3.7 |
| 11 | ANATASE $TiO_2$ (IX) of BET = 237 m²/g | 97.0 | 15.5 | 2.0 | 17.5 | 7.7 |
| 12 | ANATASE $TiO_2$ (IX) of BET = 237 m²/g calcined for 5 hours at 550° C. | 98.0 | 21.5 | 7.5 | 29.0 | 2.9 |
| 13 | ANATASE $TiO_2$ (X) of BET = 190 m²/g calcined for 3 hours at 400° C. | 99.5 | 13.5 | 4.5 | 18.0 | 3.0 |

BET = BET specific surface area

| | | |
|---|---|---|
| (i) | CR of $H_2O_2$ | 85.5% |
| (ii) | Y of pyrocatechol | 40.5% |
| (iii) | Y of hydroquinone | 25.0% |
| (iv) | Total Y of diphenols | 65.5% |
| (v) | PC/HQ ratio | 1.6. |

EXAMPLE 19

50.1 g of phenol (0.53 mol) and 0.499 g of ANATASE $TiO_2$ (IX), calcined for 1 hour and 30 minutes at 400° C. and then for 2 hours at 550° C., were charged into a 100 cm³ Pyrex glass reactor fitted with a central stirrer, a condenser connected to a gas holder, a controlled heating system and an injection system, after previously purging with nitrogen.

The mixture was heated to 80° C. under stirring, and 0.335 g of an aqueous 69.5% weight by weight $H_2O_2$ solution was then injected therein (6.85 mmol of $H_2O_2$).

The mixture was then permitted to react for 45 minutes at 80° C.

After filtering off the catalyst, unconverted $H_2O_2$ was analyzed iodometrically and the diphenols were analyzed by high-performance liquid chromatography (HPLC).

The following results were obtained:

| | | |
|---|---|---|
| (i) | CR of $H_2O_2$ | 99.5% |
| (ii) | Y of pyrocatechol | 58.0% |
| (iii) | Y of hydroquinone | 13.5% |
| (iv) | Total Y of diphenols | 71.5% |
| (v) | PC/HQ ratio | 4.3. |

EXAMPLE 20

47.0 g of phenol (0.5 mol) and 0.5 g of ANATASE $TiO_2$ (IX), calcined for 1 hour and 30 minutes at 400° C. and then for 2 hours at 550° C., were charged into a 100 cm³ Pyrex glass reactor fitted with a central stirrer, a condenser connected to a gas holder, a controlled heating system and an injection system, after previously purging the apparatus with nitrogen.

The mixture was heated to 80° C. under stirring and 1.287 g of an aqueous 70% weight by weight $H_2O_2$ solution were then injected therein (26.5 mmol of $H_2O_2$).

The mixture was then permitted to react for 10 minutes at 80° C.

After filtering off the catalyst, unconverted $H_2O_2$ was analyzed iodometrically and the diphenols were analyzed by high-performance liquid chromatography (HPLC).

The following results were obtained:

| | | |
|---|---|---|
| (i) | CR of $H_2O_2$ | 93.5% |
| (ii) | Y of pyrocatechol | 40.0% |
| (iii) | Y of hydroquinone | 7.0% |
| (iv) | Total Y of diphenols | 47.0% |
| (v) | PC/HQ ratio | 5.9. |

EXAMPLE 21

47.0 g of phenol (0.5 mol) and 0.5 g of ANATASE $TiO_2$ (IX), calcined for 1 hour and 30 minutes at 400° C. and then for 2 hours at 550° C., were charged into a 100 cm³ Pyrex glass reactor fitted with a central stirrer, a condenser connected to a gas holder, a controlled heating system and an injection system, after previously purging the apparatus with nitrogen.

The mixture was heated to 110° C. under stirring and 1.287 g of an aqueous 70% weight by weight $H_2O_2$ solution were then injected therein (26.5 mmol of $H_2O_2$).

The mixture was then permitted to react for 5 minutes at 110° C.

After filtering off the catalyst, unconverted $H_2O_2$ was analyzed iodometrically and the diphenols were analyzed by high-performance liquid chromatography (HPLC).

The following results were obtained:

| | | |
|---|---|---|
| (i) | CR of $H_2O_2$ | 98.0% |
| (ii) | Y of pyrocatechol | 34.0% |
| (iii) | Y of hydroquinone | 9.0% |
| (iv) | Total Y of diphenols | 43.0% |
| (v) | PC/HQ ratio | 3.8. |

EXAMPLE 22

The procedure of Example 21 was repeated, but carrying out the reaction at 150° C.

The following results were obtained:

| | | |
|---|---|---|
| (i) | CR of $H_2O_2$ | 100% |
| (ii) | Y of pyrocatechol | 22.0% |
| (iii) | Y of hydroquinone | 8.5% |
| (iv) | Total Y of diphenols | 30.5% |
| (v) | PC/HQ ratio | 2.6. |

EXAMPLES 23 TO 25

4.7 g of phenol (0.05 mol), 0.1 g of ANATASE $TiO_2$ (IX), calcined for 1 hour and 30 minutes at 400° C. and then for 2 hours at 550° C., and 4.7 g of solvent (see Table 3 below) were charged into a 30 cm³ Pyrex glass reactor fitted with a central bar magnet stirrer, a condenser connected to a gas holder, a controlled heating system and an injection system, after previously purging the apparatus with nitrogen.

The mixture was heated to 80° C. under stirring and an aqueous 70% weight by weight $H_2O_2$ solution was then injected therein (0.0025 mol of $H_2O_2$).

The mixture was permitted to react for 2 hours and 30 minutes.

After filtering off the catalyst, unconverted $H_2O_2$ was analyzed iodometrically and the diphenols were analyzed by high-performance liquid chromatography (HPLC).

The results obtained are reported in Table 3 below.

TABLE 3

| EXAMPLES | SOLVENTS | % CR of $H_2O_2$ | % Y of PC | % Y of HQ | % Y of diphenols | PC/HQ ratio |
|---|---|---|---|---|---|---|
| 23 | Acetonitrile | 97.5 | 40.0 | 11.5 | 51.5 | 3.4 |
| 24 | Ethanol | 97.5 | 28.5 | 14.5 | 43.0 | 1.9 |
| 25 | Methyl tert.-butyl ether | 95.5 | 42.5 | 11.5 | 54.0 | 3.7 |

EXAMPLES 26 and 27

9.4 g of phenol (0.10 mol) and 0.1 g of ANATASE titanium dioxide (IX), calcined for 3 hours at different temperatures, were charged into a 30 cm³ Pyrex glass reactor fitted with a central bar magnet stirrer, a condenser connected to a gas holder, a controlled heating system and an injection system, after previously purging the apparatus with nitrogen.

The mixture was heated to 80° C. under stirring and an aqueous 70% weight by weight $H_2O_2$ solution was then injected therein (0.0050 mol of $H_2O_2$).

The mixture was then permitted to react for 10 minutes at 80° C.

After filtering off the catalyst, unconverted $H_2O_2$ was analyzed iodometrically and the diphenols were analyzed by high-performance liquid chromatography (HPLC).

The results obtained are reported in Table 4 below.

TABLE 4

| EXAMPLES | CALCINATION TEMPERATURE | % CR of $H_2O_2$ | % Y of PC | % Y of HQ | % Y of diphenols | PC/HQ ratio |
|---|---|---|---|---|---|---|
| 26 | 400° C. BET 122 M²/G* | 99.0 | 42.5 | 10.0 | 52.5 | 4.2 |
| 27 | 700° C. BET 37 M²/G* | 78.5 | 32.0 | 6.5 | 38.5 | 4.9 |

*BET = BET specific surface area

EXAMPLES 28 TO 30

9.4 g of phenol (0.10 mol) and 0.1 or 0.25 g of ANATASE titanium dioxide (IX), calcined for 3 hours at different temperatures, were charged into a 30 cm³ Pyrex glass reactor fitted with a central bar magnet stirrer, a condenser connected to a gas holder, a controlled heating system and an injection system, after previously purging the apparatus with nitrogen.

The mixture was heated to 80° C. under stirring and an aqueous 70% weight by weight $H_2O_2$ solution was then injected therein (0.0050 mol of $H_2O_2$).

The mixture was then permitted to react for 2 hours and 30 minutes at 80° C.

After filtering off the catalyst, unconverted $H_2O_2$ was analyzed iodometrically and the diphenols were analyzed by high-performance liquid chromatography (HPLC).

The results obtained are reported in Table 5 below.

TABLE 5

| EXAMPLES | CALCINATION TEMPERATURE | % CR of $H_2O_2$ | % Y of PC | % Y of HQ | % Y of diphenols | PC/HQ ratio |
|---|---|---|---|---|---|---|
| 28* | 700° C. BET 37 m²/g | 92.5 | 23.5 | 7.0 | 30.5 | 3.3 |
| 29** | 850° C. BET 7 m²/g | 57.0 | 21.5 | 3.5 | 25.0 | 6.1 |
| 30** | 1,000° C. BET 2.5 m²/g | 52.0 | 13.5 | 3.0 | 16.5 | 4.5 |

*0.1 g of $TiO_2$
**0.25 g of $TiO_2$

EXAMPLES 31 TO 35

47 g of phenol (0.50 mol) and 1 g titanium dioxide (GEL G5 NC 079 marketed by THANN ET MULHOUSE Co.), calcined for 3 hours at 400° C., 47 g of a solvent (Table 6), were charged into a 100 cm³ Pyrex glass reactor fitted with a central stirrer, a condenser connected to a gas holder, a controlled heating system and an injection system, after previously purging the apparatus with nitrogen.

The mixture was heated to 80° C. under stirring and an aqueous 70% weight by weight $H_2O_2$ solution was then injected therein over 2 minutes (0.025 mol of $H_2O_2$).

The mixture was then permitted to react for 2 hours at 80° C.

After filtering off the catalyst, unconverted $H_2O_2$ was analyzed iodometrically and the diphenols were analyzed by high-performance liquid chromatography (HPLC).

The results obtained are reported in Table 6 below.

TABLE 6

| EXAMPLES | SOLVENTS | % CR of $H_2O_2$ | % Y of PC | % Y of HQ | % Y of diphenols | PC/HQ ratio |
|---|---|---|---|---|---|---|
| 31 | Acetonitrile | 94.6 | 46.3 | 11.3 | 57.6 | 4.1 |
| 32 | tert.-butanol | 98.5 | 46.8 | 14.8 | 61.6 | 3.2 |
| 33 | Methyl tert.-butyl ether | 96.9 | 49.4 | 12.1 | 61.5 | 4.1 |
| 34 | Acetone | 95.3 | 43.2 | 18.5 | 61.7 | 2.3 |
| 35 | Methyl isobutyl ketone | 97.0 | 42.2 | 10.5 | 52.7 | 4.0 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

WHAT IS CLAIMED IS:

1. A process for the preparation of an hydroxylated phenol or phenol ether, or an admixture thereof comprising reacting a compound of the formula (I):

in which $R_1$ is a hydrogen atom, or a methyl, ethyl or phenyl radical, and $R_2$ is a hydrogen atom, an alkyl radical having from 1 to 4 carbon atoms, an alkoxy radical having from 1 to 4 carbon atoms, or a phenyl or cyclohexyl radical with hydrogen peroxide, in the presence of a catalytically effective amount of a catalyst consisting essentially of titanium dioxide.

2. The process as defined by claim 1, wherein formula (I) $R_1$ is a hydrogen atom, or a methyl or ethyl radical, and $R_2$ is a hydrogen atom, a methyl, ethyl or tert-butyl radical or a methoxy or ethoxy radical.

3. The process as defined by claim 1, said compound of the formula (I) comprising phenol, anisole, orthocresol, metacresol, paracresol, 4-tert.-butylphenol, 2-methoxyphenol or 4-methoxyphenol.

4. The process as defined by claim 1, carried out discontinuously, in the presence of from 0.1% to 20% by weight of titanium dioxide relative to the weight of the compound of formula (I).

5. The process as defined by claim 1, carried out continuously over a fixed bed of said titanium dioxide.

6. The process as defined by claim 1, said titanium dioxide comprising anatase titanium dioxide, rutile titanium dioxide, or brookite titanium dioxide.

7. The process as defined by claim 1, said titanium dioxide having been pre-calcined for one to several hours at a temperature ranging from about 300° C. to 1,000° C.

8. The process as defined by claim 1, wherein the molar ratio of the compound of formula (I)/hydrogen peroxide ranges from 25/1 to 3/1.

9. The process as defined by claim 1, said hydrogen peroxide comprising an aqueous solution thereof.

10. The process as defined by claim 1, said hydrogen peroxide comprising an organic solution thereof.

11. The process as defined by claim 1, carried out in a solvent for the compound of the formula (I).

12. The process as defined by claim 1, carried out at a temperature ranging from 45° C. to 160° C.

13. The process as defined by claim 1, said titanium dioxide comprising a powder or shaped article thereof.

14. The process as defined by claim 4, carried out in the presence of from 0.5% to 10% by weight of titanium dioxide relative to the weight of the compound of formula (I).

15. The process as defined by claim 7, said titanium dioxide having been pre-calcined at a temperature ranging from 300° C. to 700° C.

16. The process as defined by claim 8, said molar ratio ranging from 20/1 to 4/1.

17. The process as defined by claim 11, said solvent being at least partially miscible with water.

18. The process as defined by claim 17, said solvent comprising water, an alcohol, a ketone, a nitrile, a carboxylic acid, an ester, an ether, or a polar aprotic solvent.

19. The process as defined by claim 13, said shaped article comprising pellets, spheres or a monolith.

20. The process as defined by claim 1, comprising the preparation of an admixture of pyrocatechol and hydroquinone.

* * * * *